United States Patent [19]
Perneborn

[11] Patent Number: 5,415,717
[45] Date of Patent: May 16, 1995

[54] METHOD AND APPARATUS FOR DEPOSITING PARTICLES ON A MOVING WEB OF MATERIAL

[75] Inventor: Robert Perneborn, Göteborg, Sweden

[73] Assignee: Mölnlycke AB, Göteborg, Sweden

[21] Appl. No.: 137,130

[22] PCT Filed: Apr. 24, 1992

[86] PCT No.: PCT/SE92/00271

§ 371 Date: Oct. 22, 1993

§ 102(e) Date: Oct. 22, 1993

[87] PCT Pub. No.: WO92/19198

PCT Pub. Date: Nov. 12, 1992

[30] Foreign Application Priority Data

Apr. 24, 1991 [SE] Sweden .................. 9101239

[51] Int. Cl.6 .............................................. B32B 31/00
[52] U.S. Cl. ..................... 156/276; 156/277; 156/290; 427/345; 427/197; 427/282; 118/301; 118/308; 118/325
[58] Field of Search ................. 156/62.2, 277, 276, 156/279, 290; 427/188, 345, 197, 282, 424; 118/301, 308, 325; 425/80.1

[56] References Cited

U.S. PATENT DOCUMENTS 2,949,646  8/1960  Clark ................... 425/80.1
3,868,287  2/1975  Lewyckyj ............. 156/290
4,538,486  4/1986  Miller .................. 118/308
4,800,102  1/1989  Takada ................. 427/197
5,118,376  6/1992  Pigneul ................ 156/292

FOREIGN PATENT DOCUMENTS

WO87/00057  1/1987  WIPO .

Primary Examiner—Chester T. Barry
Attorney, Agent, or Firm—Burns, Doane, Swecker & Mathis

[57] ABSTRACT

An arrangement for depositing particles onto a moving material web includes a particle dispenser and a perforated belt which moves over the material web. According to the invention, the particle dispenser is intended to dispense particles continuously in a uniform and wide flow whose width is equal to or somewhat greater than the width of the hole-pattern of the belt and the belt is spaced at a distance from the material web which is at least sufficiently large for the particles deposited on the material web to be accommodated between the belt and the web. The arrangement also includes means which function to remove particles caught by the belt without the particles falling down onto the underlying material web. These means are located downstream of the particle dispenser. The invention also relates to a method for depositing particles to a moving material web.

24 Claims, 3 Drawing Sheets

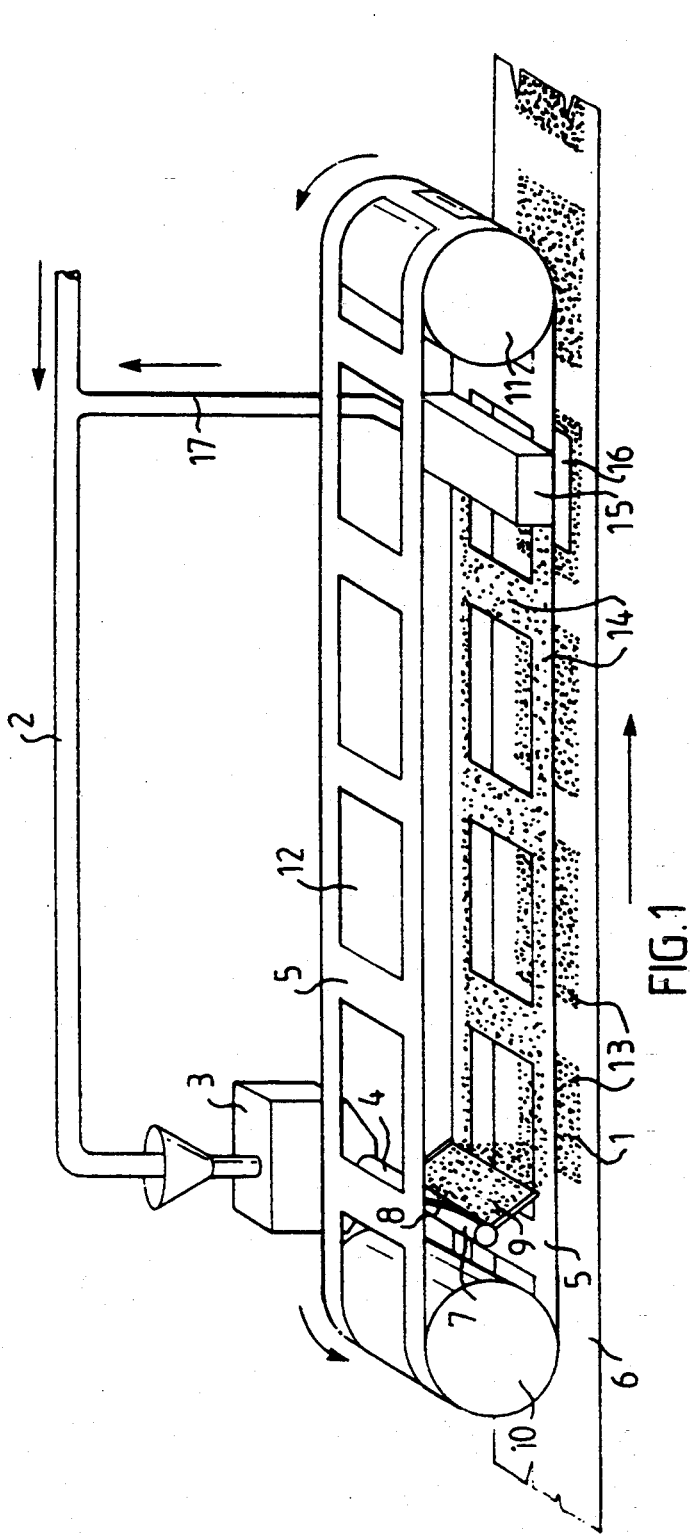
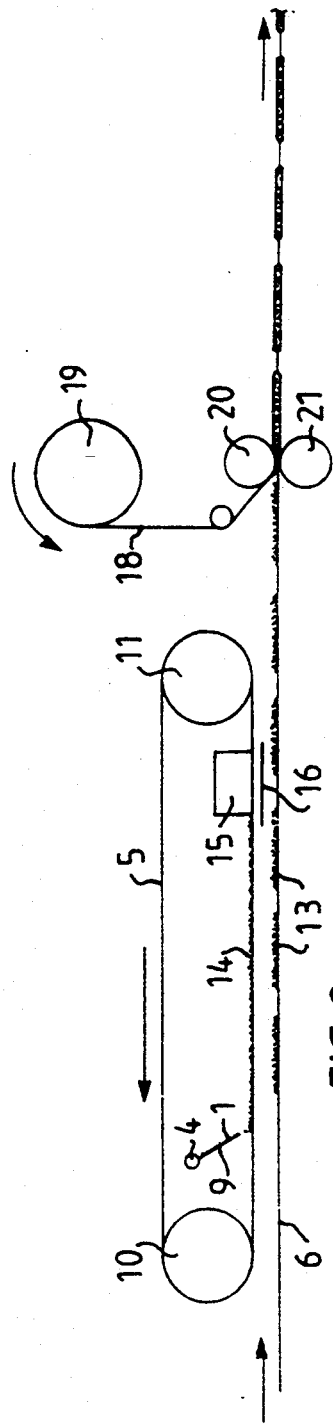
FIG.1
FIG.2

METHOD AND APPARATUS FOR DEPOSITING PARTICLES ON A MOVING WEB OF MATERIAL

This application is a Section 371 continuation of PCT/SE92/00271, filed Apr. 24, 1992.

BACKGROUND OF THE INVENTION

1. Field of the Invention

The present invention relates to a method and to apparatus for depositing particles on a moving web of material through the intermediary of a perforated belt which moves over the web.

2. Description of Related Art

The absorbent material used in disposable absorbent products, such as diapers, sanitary napkins, incontinence guards, wound dressings and the like, is normally comprised mainly of absorbent fibres, such as cellulose fibres. Absorbent bodies, or pads, which are comprised mainly of cellulose fibres have certain drawbacks, however. For instance, the ability of such bodies to retain the liquid absorbed is poor, particularly when the absorbent body is subjected to load or pressure. Furthermore, the total capacity of such absorbent bodies to absorb liquid is restricted and such bodies quickly become saturated despite the good liquid-spreading, or liquid-dispersing properties of the fibres.

With the intention of overcoming these drawbacks, there has been developed an absorbent material which has a much greater absorbency than cellulose fibres. These so-called superabsorbents are polymers whose liquid absorption capacity is many times the intrinsic weight of the polymers. Although superabsorbents have good liquid retention abilities, they are unable to spread or disperse liquid to the same good extent. Furthermore, superabsorbents swell while absorbing liquid, thereby forming gels which are liable to deny the liquid access to still unused absorbent material. This may result in so-called gel blockaging.

Superabsorbents may be comprised of different types of polymers and are produced in several different forms, for instance in film or particle forms. This latter form is often used for superabsorbents which are intended as absorbent material for use in disposable diapers, for instance. By "particle form" is meant here all types of material which exist in powder, flake, granular, short-fibre form and like forms.

Different methods for introducing particulate superabsorbents into absorbent bodies have been proposed. "Particulate superabsorbents" will be referred to in the following as "superabsorbent particles" or simply as "particles".

WO 87/00057 teaches a method and an arrangement of apparatus of the kind mentioned in the introduction for forming cavities in a moving fibre web with the aid of a roll provided with a pattern of outwardly-protruding teeth, wherein the cavities thus formed are filled with superabsorbents. The superabsorbents are delivered to the fibre web intermittently, by means of a particle feeder or dispenser mounted above the fibre web, and a scraper which is mounted downstream of the particle feeder and which functions to move those particles which have landed outside the cavities down thereinto. The superabsorbent particles introduced into the cavities are then pressed against the cavity bottom by a second toothed roller having the same tooth pattern as the first roller. The two rollers must therefore be driven exactly synchronously in relation to one another and to the underlying fibre web, in order for the teeth of the latter roller to enter the cavities formed by the teeth of the first roller, and to this end the arrangement includes a drive belt which is provided with a hole-pattern corresponding to the tooth pattern of the rollers and which is intended to pass around said rollers. The drive belt is also arranged for abutment with the fibre web, so as to ensure that no superabsorbent particles will land on the upper side thereof. This known arrangement can therefore not be used to deliver a layer of superabsorbent particles to the upper surface of a material web.

Another method is one of mixing the particles with pulp fibres in the air flow which enters the former. This results in a more or less homogenous mixture of cellulose fibres and superabsorbent particles.

Another method of introducing superabsorbent particles into absorbent bodies involves layering the particles on a material web. This web may be moveable and may be comprised, for instance, of cellulose fluff, tissue, non-woven fabric or the like. The layer of superabsorbent material may then be covered with a further web of material, if desired. Different types of binder can be used to bind the particles firmly to the material web, for instance water or steam. None of the methods known at present for laying superabsorbent particles onto a moving material web will enable sharply defined, discrete particle regions to be obtained when the web is moving at a high speed. This is disadvantageous, of course, since a high production rate is highly significant to production volume.

For instance, it has been proposed to strew superabsorbent particles onto a passing material web, via a rotating roller. An attempt has been made to cover discrete areas or regions of the web with particles, by alternately starting and stopping the roller. An alternative method involves the arrangement of discrete hollows on the peripheral surface of the roller from which superabsorbent particles can be strewn onto the passing web as the roller rotates. None of these methods can be applied satisfactorily in practice at high web speeds when desiring the creation of discrete patterns of application in the form of sharply defined particle regions in absorbent bodies. Neither do these known methods enable their application patterns to be modified or changed in a simple and quick fashion.

OBJECTS AND SUMMARY

An object of the present invention is to overcome the aforesaid drawbacks by means of a method which will enable superabsorbent particles to be disposed continuously in a specific, well-defined and discretely arranged pattern on the Upper surface of a material web which moves at a relatively high speed.

An inventive method is mainly characterized by feeding the particles continuously from a particle feeder or dispenser in a uniform and wide flow whose width is equal to or slightly greater than the width of the hole-pattern of the web; depositing the particles to the material web in discrete layers with uniformly distributed particles, the configuration of each layer being determined by the configuration of respective holes; and removing from the belt those particles that are caught thereon without said particles falling down onto the underlying material web and without disturbing the discrete particle layers applied to said web by said removal of said particles.

These advantages afforded by the inventive method are that sharply defined, discontinuous particle regions of uniform particle distribution can be obtained in layers of particles produced continuously on a moving material web.

Furthermore, superabsorbent particles can be laid with good precision and reproduceability on a material web which moves at high speed.

Another advantage is that the configuration of the particle-covered regions can be changed readily and quickly, by changing the perforated belt or masking web for another belt or web.

An inventive arrangement for delivering particles to a moving material web comprises a particle dispenser and a perforated belt which moves over the material web. The arrangement is characterized in that the particle dispenser is constructed to dispense particles continuously in a uniform and wide stream, the width of which is equal to or slightly greater than the width of the hole-pattern of the belt; in that the belt is spaced from the material web; by a distance which is at least sufficiently large to accommodate the layer of particles between said belt and said web; and in that the arrangement includes means for removing particles that have been caught by the belt without said particles falling down onto the underlying material web, said means being located downstream of the particle feeder.

This arrangement enables the thickness of the layers and the distribution of particles therein to be varied, by varying the relative speed and/or the distance between the material web and the belt, thereby rendering the arrangement extremely flexible.

BRIEF DESCRIPTION OF THE DRAWINGS

The invention will now be described in more detail with reference to exemplifying embodiments thereof illustrated in the accompanying drawings.

FIG. 1 is a perspective view of one embodiment of an inventive arrangement intended for layering particles on a moving web of material.

FIG. 2 is a schematic side view of the same embodiment as that illustrated in FIG. 1.

DETAILED DESCRIPTION OF PREFERRED EMBODIMENTS

Figure 3:
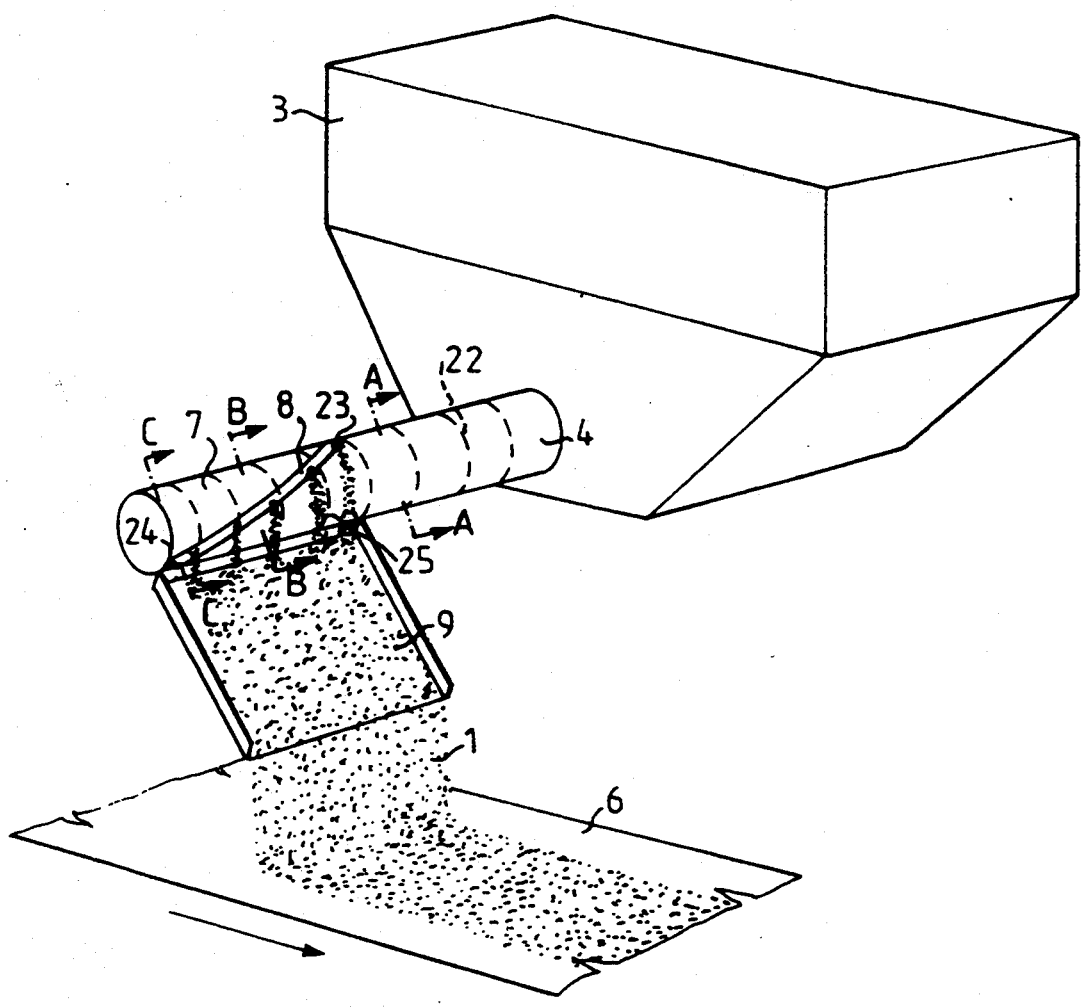
FIG. 3 illustrates a particle dispenser included in the arrangement illustrated in FIGS. 1 and 2.

FIG. 1 illustrates the transportation of superabsorbent particles 1 from a depot (not shown) through a transport conduit 2, for instance a pipe, to a dispensing device 3, for instance a screw dispenser. The particles 1 are then fed from the dispenser 3, via a screw device 4, down onto the masking web or perforated belt 5 moving therebeneath, and down onto a first material web 6 which travels beneath the masking web 5.

The masking web 5 and the first material web 6 preferably move at the same speed and in the same direction. The outlet part 7 of the screw device 4 roughly defines a right angle with the direction of movement of the webs 5, 6. The outlet part 7 is comprised of a slot 8 which extends in the longitudinal direction of the screw device 4 and which is formed in the outer casing of said screw device. The screw device 4 and its outlet part 7 will be described in more detail with reference to FIGS. 3–6 below. In order to understand the FIG. 1 illustration, however, it is mentioned now that the particles 1 are dispensed through the slot 8 in the outlet part 7 as the screw rotates, and that the width of the thus dispensed flow of particles in relation to the movement direction of the webs 5, 6 is determined by the length of the slot 8.

This width-defined particle-flow is fed down onto a sloping surface 9 and the particles 1 falling down from the slot are distributed uniformly across the width of said surface prior to falling down onto the masking web 5 in the form of a uniform curtain of particles.

The masking web 5 is comprised of an endless belt which moves in a path around two forward drive rolls 10, 11 in the direction of the arrows shown. The drive source and associated drive mechanism are not shown in FIG. 1.

The masking web 5 has formed therein a plurality of identical holes 12 through which a large number of the particles 1 fall down onto the first material web 6 moving beneath the masking web 5, said particles 1 being deposited in specific, discrete regions 13 whose configuration and size coincide with the configuration and size of the holes 12 in the masking web 5. A number of particles 14, however, will remain on the masking web 5, namely those particles which fall onto the space between the holes 12 and those which fall onto side areas of said holes. These particles 14 accompany the masking web 5 and are removed therefrom by means of a suction device 15 located upstream of the forward drive roll 11, which is mounted downstream of the particle dispenser 3. In order to prevent removal by suction of those particles 1 which have been deposited on the first material web 6, a screen 16, or some like device, is mounted between the webs 5, 6 beneath the suction device 15. The particles 14 removed by the suction device are returned to the transport conduit 2, through a further transport conduit 17, and from there to the dispenser 3. As will be understood, the transport conduits 17 through which the particles 14 removed by said suction device are conveyed may lead directly to the dispenser 3 or back to the depot. Alternatively, means for returning the particles 14 removed by said suction device may be dispensed with and production carried out with solely the removal of these particles from the masking web 5.

The masking web 5 turns around the forward drive roll 11 and moves back above the suction device 15 and the screw device 4 and finally turns around the forward drive roll 10, thus completing a full cycle.

The size and the shape of the holes 12 is optional. The holes 12 shown in FIG. 1 are rectangular in shape, although other shapes are conceivable, of course, such as circular, elliptical or triangular hole patterns or combinations thereof. In the FIG. 1 embodiment, the holes 12 are arranged sequentially, although it will be understood that two or more holes may be arranged in the width direction and may also be displaced relative to one another in the longitudinal direction of the web. The masking web 5 is made of particle-impenetrable material, for example a fabric-reinforced polymer band.

FIG. 2 illustrates schematically the same process as that illustrated in FIG. 1. The transport conduits 2, 17 and the dispenser 3 are not shown in the drawing, however. FIG. 2 illustrates the process stage in which the first material web 6 passes beneath the suction device 15, the screen 16 and the forward drive roll 11 of the masking web 5, subsequent to having deposited particles on the first material web 6. A second material web 18 is advanced from a reel 19 and is brought into contact with the first material web 6 such that the particle regions 13 will be covered by the second web 18. The combined webs 6, 18 are moved in between two compression rolls 20, 21, thereby locking the particles 1 firmly between the two webs 6, 18 by compression.

The compressing process can be completed with other methods which are known to firmly lock the superabsorbent particles together, for instance methods which involve the use of binder coatings or spraying of the particles and/or material webs with water or steam.

Upon exiting from the compression rolls 20, 21, the material webs 6, 18 are conveyed to following process stages (not shown), which may involve folding and cutting of the webs to form individual absorbent bodies. It is also conceivable to cover the first and the second material webs 6, 18 with additional particle-coated material webs prior to said following process stages, in order to create several separate, superimposed particle regions. These additional material webs may suitably be coated with particles in the same manner as the material webs 6, 18 of the FIG. 2 embodiment. The material webs may comprise webs of, e.g., cellulose fluff, tissue, non-woven fabric or perforated plastic.

As will be seen from FIGS. 1 and 2, the masking web 5 is spaced from the material web 6. In order to obtain sharp and well-defined edges around the applied particle layers 13, the distance between said webs should not exceed 100 mm and will preferably be shorter than 15 mm. This distance must also be sufficient to ensure that the particle layers 13 will pass freely from the masking web 5 and freely from the screen 16. It will be understood, however, that the shorter the distance between the web 5 and the material web 6 the greater the risk of diffuse edges around the layers 13. In order to ensure that this distance can be made as short as possible, the material web 6 may be permitted to move in a path which is slightly inclined to the masking web 5, such that the part of the web 5 at which the suction device 15 and the screen 16 are placed will be located at a greater distance from the material web 6 than is that part of the web at which the particle dispenser is placed. It is preferred, however, that the masking web 5 and the material web 6 extend parallel with one another and move at the same speed, so that those superabsorbent particles which may fall down through any of the holes 12 from the masking web from that part of the web 5 which moves between the particle dispenser and the suction device will definitely fall down onto the material web 6 into one of the particle layers 13 already laid on said web. Particles which land outside these layers are liable to damage the clipping or cutting tools used to cut the material webs 6, 18 into individual absorbent products. For the same reason, it is preferred that the web 5 will move in the same direction as the material web 6. It is thus important to ensure that no particles will land outside the edges of the particle layers 13.

It will be understood from the aforegoing that when wishing to utilize the possibility of varying the extension of the particle layers, by varying the speed at which the masking web 5 moves in relation to the material web 6, the masking web should be configured so that particles which land around the edges of the holes 12 in the section of the web 5 located between the particle dispenser and the suction device 15 will be retained on said edges, for instance by providing the web 5 with a rough surface. From the aspect of safety, a web of this configuration is also suitable in the earlier described operating conditions.

The illustrated embodiment of the inventive arrangement has been tested with a spacing between the material web 6 and the masking web 5 of from 5–15 mm. When operating the arrangement within this spacing range, it has been found that the particle layers 13 will have well-defined, sharp edges beth immediately after being deposited and also after having passed the suction device 15.

FIG. 3 illustrates dispensing of particles 1 and the laying of said particles on the first material web 6 in more detail. For the sake of illustration, the masking web and the forward drive roll 10 have been omitted from the Figure.

The particles 1 are dispensed from the dispenser 3 by means of the screw device 4 and its screw 4'. A vibratory device may be coupled to the screw device in order to facilitate dispensing of the particles.

The threads 22 of the screw 4' are shown in broken lines. The outlet part 7 is comprised of a longitudinally extending part of the screw device 4, in which a slot 8 has been formed in the outer casing of said device. The slot is of an elongated-arcuate shape and extends from a highest position 23 at the beginning of the outlet part 7, to a lowest position 24 at the end of said outlet part. The arcuate shape is adapted to the transportation properties of the particles, i.e. in accordance with their ability to run or flow. The slot 8 need not be arcuate, however, but may be linear instead. The inclination of the slot is contingent on the length of the outlet part. As the screw rotates, particles are transported forwardly towards the outlet part 7, whereafter the particles are dispensed successively through the slot 8. This is shown in detail in FIGS. 4–6.

Figure 4:
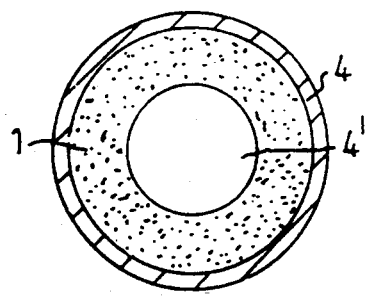
FIG. 4 is a sectional view taken on the line A—A in FIG. 3.
Figure 5:
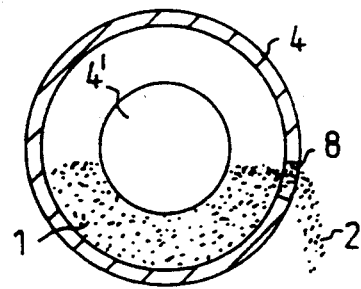
FIG. 5 is a sectional view taken on the line B—B in FIG. 3.

FIG. 4 illustrates how the particles 1 are advanced in the screw device 4 in a stage prior to having reached the outlet part 7 and therewith the slot 8. In the FIG. 5 illustration, the screw 4' has advanced the particles 1 to a point equal to roughly half the length of the slot, wherein roughly half of the particles having already been dispensed.

Figure 6:
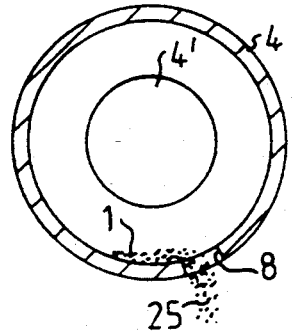
FIG. 6 is a sectional view taken on the line C—C in FIG. 3.

FIG. 6 shows the particles located almost at the outermost, and therewith the lowest position 24 of the slot 8, in which position the last particles 1 are also fed from the screw 4'.

Thus, a number of particle flows 25 are dispensed from the screw device 4 and fall down onto the inclined surface 9. These particle flows are mixed across the width of the inclined surface into a single more or less uniformly distributed particle flow which falls down in the form of a curtain onto and through the masking web 5 (not shown) and thereafter onto the first material web 6.

The invention shall not be considered limited to the described and illustrated embodiments thereof, since a number of variants are conceivable within the scope of the following Claims.

For example, it is conceivable for the screw device to be angled in relation to the masking web instead of being straight.

The slot in the particle dispenser may also be divided into a longitudinally extending row of small slots which are mutually separated by residual parts of the outer casing of the dispenser.

It is also possible, of course, to remove superfluous particles from the masking web in a manner other than by suction. For example, these particles may be brushed or scraped away with the aid of appropriate means.

Although the invention has been described with reference to the use of superabsorbent particles, it will be understood that the invention can also be applied with other particulate material which is to be applied in specific, discrete regions on a material web. An example of such different material is fragmented thermoplastic material.

I claim:

1. An arrangement for depositing particles onto a moving material web, said arrangement comprising:
   a particle dispenser;
   a perforated belt which moves over the material web;
   the particle dispenser includes means for dispensing the particles continuously in a uniform and wide flow whose width is equal to or greater than the width of a hole-pattern of the belt;
   the perforated belt extends in a same direction as the material web;
   the belt is spaced from the material web at a distance which is at least sufficient to accommodate the particles deposited on the material web between said belt and said web; and
   the arrangement includes means for removing particles which have been caught by the belt without the particles falling down onto the underlying material web, said means being located downstream of the particle dispenser.

2. The arrangement of claim 1, further comprising a screw device in the particle dispenser for uniformly distributing the particles over the moving web.

3. An arrangement according to claim 1, wherein the means for removing particles caught by the belt include a suction device which is mounted immediately above the particle-coated part of the belt downstream of and at a distance from the particle dispenser, and a screen which is mounted beneath the belt at the location of the suction device such as to shield the material web from the influence of the suction device.

4. An arrangement according to claim 3, wherein the belt moves past the means for removing particles caught by the belt at a greater distance from the material web than at the location of the particle dispenser.

5. An arrangement according to claim 3, wherein the perforated belt has a rough surface on that side thereof on which particles are caught.

6. An arrangement according to claim 5, wherein the belt moves past the means for removing particles caught by the belt at a greater distance from the material web than at the location of the particle dispenser.

7. An arrangement according to claim 1, wherein the perforated belt has a rough surface on that side thereof on which particles are caught.

8. An arrangement according to claim 7, further comprising means for varying the relative speed between the perforated belt and the material web.

9. An arrangement according to claim 8, wherein the belt moves past the means for removing particles caught by the belt at a greater distance from the material web than at the location of the particle dispenser.

10. An arrangement according to claim 7, wherein the belt moves past the means for removing particles caught by the belt at a greater distance from the material web than at the location of the particle dispenser.

11. An arrangement according to claim 1, wherein the belt moves past the means for removing particles caught by the belt at a greater distance from the material web than at the location of the particle dispenser.

12. A method for depositing particulate material onto a moving web of fibrous material through the intermediary of a perforated masking belt which moves at a distance above said web, so as to deposit the particulate material onto the web of fibrous material in discrete layers of uniformly distributed particles, comprising the steps of:
    driving the perforated belt in a same direction as the underlying web of fibrous material;
    dispensing the particles continuously from a particle dispenser in a uniform flow whose width is equal to or greater than a width of holes in the masking belt, so that the particulate material falls down through the holes in the masking belt and deposits on the web of fibrous material in a configuration corresponding to a hole pattern in the masking belt; and
    removing from the masking belt those particles which have been caught by said belt without falling down onto the underlying web of fibrous material and without said removal having a disturbing influence on the discrete particle layers deposited on said web of fibrous material.

13. A method according to claim 12, characterized by driving the perforated belt at the same speed.

14. A method according to claim 13, further comprising placing a second material web on top of the material web on which discrete layers of particles have been deposited and then joining the two material webs together by compression.

15. A method according to claim 12, characterized by driving the perforated belt and the material web at different speeds.

16. A method according to claim 15, further comprising placing a second material web on top of the material web on which discrete layers of particles have been deposited and then joining the two material webs together by compression.

17. A method according to claim 12, further comprising placing a second material web on top of the material web on which discrete layers of particles have been deposited and then joining the two material webs together by compression.

18. The method of claim 12, further comprising the step of using a screw device to uniformly distribute the particles.

19. A method of making a composite material that includes a fibrous material with particulate material thereon, comprising the steps of:
    moving a web of fibrous material in a given direction;
    driving a masking belt having a plurality of perforations in a hole pattern therein in the given direction at a distance above said fibrous material;
    depositing in a uniform flow a layer of particulate material onto the masking belt, said uniform flow having a width that equals or exceeds a width of the perforations so that the particulate material falls down through the perforations in the masking belt and is deposited on the fibrous material in a configuration corresponding to the hole pattern in the masking belt; and
    removing from the masking belt the particulate material which has been caught by the masking belt without disturbing the particulate material deposited on said fibrous material.

20. The method of claim 19, wherein the web of fibrous material and the masking belt move at the same speed.

21. The method of claim 19, wherein the web of fibrous material and the masking belt move at different speeds.

22. The method of claim 19, further comprising the step of placing a second fibrous material on top of the web of fibrous material on which the particulate material has been deposited and then joining the two fibrous materials together by compression.

23. The method of claim 19, further comprising the steps of:
   providing a screen between the masking belt and the fibrous material at a location downstream from a location wherein the particulate material is deposited on the fibrous material; and
   removing the particulate material from the masking belt with a suction device where the masking belt passes over the screen.

24. The method of claim 19, further comprising the step of using a screw device to evenly distribute the particulate material over the width of the uniform flow.

* * * * *